US00PP26408P3

(12) United States Plant Patent
McGhie

(10) Patent No.: US PP26,408 P3
(45) Date of Patent: Feb. 9, 2016

(54) GINGER PLANT NAMED 'MCGHIEJCG'

(50) Latin Name: *Alpinia afficinarum*
Varietal Denomination: McghieJCG

(71) Applicant: Zon International Holdings US, Inc., Carson City, NV (US)

(72) Inventor: Errol Anthony McGhie, Bog Walk (JM)

(73) Assignee: Zon International Holdings US, Inc., St Catherine (JM)

( * ) Notice: Subject to any disclaimer, the term of this patent is extended or adjusted under 35 U.S.C. 154(b) by 99 days.

(21) Appl. No.: 13/999,601

(22) Filed: Mar. 12, 2014

(65) Prior Publication Data

US 2014/0289916 P1 Sep. 25, 2014

Related U.S. Application Data

(60) Provisional application No. 61/804,302, filed on Mar. 22, 2013.

(51) Int. Cl.
*A01H 5/12* (2006.01)
*A01H 5/00* (2006.01)

(52) U.S. Cl.
USPC ..... Plt./258
CPC ..... *A01H 5/00* (2013.01)

(58) Field of Classification Search
USPC ..... Plt./258
See application file for complete search history.

*Primary Examiner* — Susan McCormick Ewoldt
(74) *Attorney, Agent, or Firm* — Klarquist Sparkman, LLP

(57) ABSTRACT

A new plant variety of the Zingerberacae family resulting from a discovery of a mutant attached to a stool (mat) of lesser galangal (*Alpinia officinarum*) in a cultivated field and subsequently asexually reproduced from stem cuttings. The most distinguishing characteristics of this new variety are the pungent cinnamon fragrance and flavor of its leaves (tea) and its physical differences with the parent plant. The new variety has valuable commercial potential and excellent post harvest prospects.

5 Drawing Sheets

Botanical denomination: *Alpinia officinarum.*
Variety designation: 'McghieJCG'.

BACKGROUND OF INVENTION

The present invention relates to a new and distinct variety of the Zingerberacae family. The new variety is named 'McghieJCG'. The new variety originated as a discovery of a mutant attached to a stool (mat) of a lesser galangal (*Alpinia officinarum* plant rhizome in a cultivated field, cultivar unknown (commercial nursery)) situated in the suburb of the town of Bog Walk in the parish of St. Catherine, Jamaica W.I.

Closest plant in resemblance to 'McghieJCG' is its parent plant *Alpinia officinarum*. The new variety develops into a fairly large mat with well-defined pseudostems bearing medium to large lanceolate leaves.

The first viewing of the 'McghieJCG' plant was in May 2012.

The Inventor subsequently asexually reproduced the new variety at the commercial nursery in Bog Walk by means of 'stem cuttings' and subsequently reproducing over three (3) generations of new plants. The distinguishing characteristics of the new plant have been retained through successive generations.

Growth was observed at nine (9) months to be impressive, as the plants exhibited consistent stable, healthy and vigorous growth characteristics with its roots, stems and leaves (entire plant) appearing to be disease free/pest resistant for the entire period of growth.

The stable mutants were reproduced under different natural conditions; i.e., partial cover, full cover, and full sunlight employing similar cultivation practices as per the mother plant; i.e. fertile, moist, and well drained soils employing the use of organic manure and moderate watering. Plants were also cultivated in pots under full and partial cover in the open field. It was observed that the best growth occurred in plants grown in the open field with partial cover and also full cover.

It was also observed that like the mother plant the leaves of the new variety had a pungent scent. The scent in either plant however, was different, and in the case of the new variety, this was Cinnamon like.

There are also significant physical differences between the new plant and its parent.

The new plant variety is suitable for commercial plant culture because of the potential valuable compounds and properties it is expected to yield when it attains maturity given its parentage.

New compounds derived so far from ongoing research of the mother plants Jamaica grown (*Alpinia officinarum*, cultivar unknown) are unique to this variety and appear not to be present in any other varieties of *Alpiana officinarum* grown previously or currently.

As a horticultural plant, the new variety exhibits adaptability as a natural indoor and outdoor plant and also because of its versatile growth patterns when grown under different environmental conditions, in pots or open fields. Other characteristics of this new variety such as its hardiness, attractiveness and general canopy, all together recommends it as a suitable plant for commercial production for the horticultural industry.

The absence of any traces of diseases/insects/and pests at this stage of its growth if maintained will also recommend it as an important agricultural plant in various crop protection programs such as barrier crops, inter-cropping, multi-cropping and landscaping.

The plant can be grown as an herb/spice in home gardens.

BRIEF DESCRIPTION OF THE DRAWINGS

The accompanying drawings consist of color photographs showing the new plant variety form at nine months along with, the mother plant of approximate same age. Additional photographs also show sections of the commercial cultivated nursery in Bog Walk, depicting fields of asexually produced new plants and also fields of the parent plants *Alpinia officinarum*. Other pictures show indoor and outdoor potted plants of the new plant variety.

DETAILED PLANT DESCRIPTION

Figure 1:
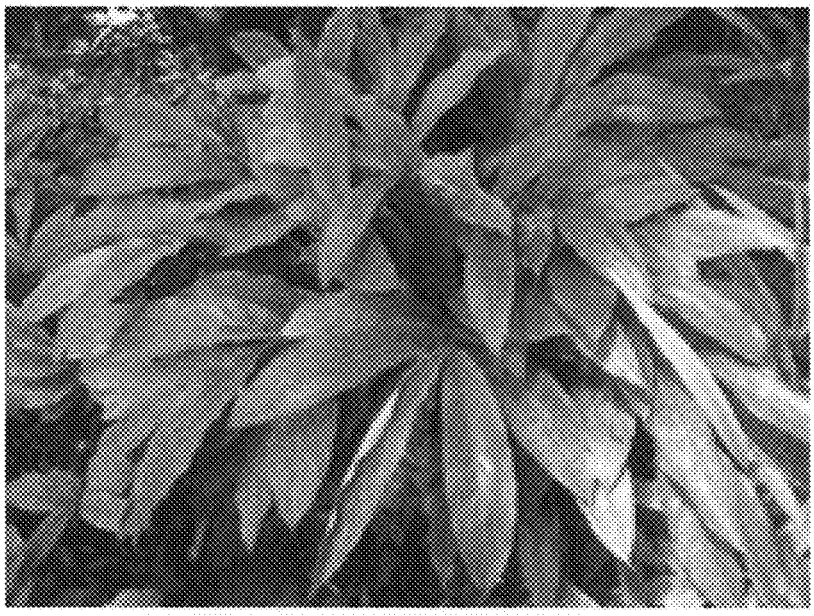
FIGS. 1-3 show a perspective view of a potted plant of the new plant variety 'McghieJCG' illustrating the overall form and appearance of the plant at nine months.
Figure 2:
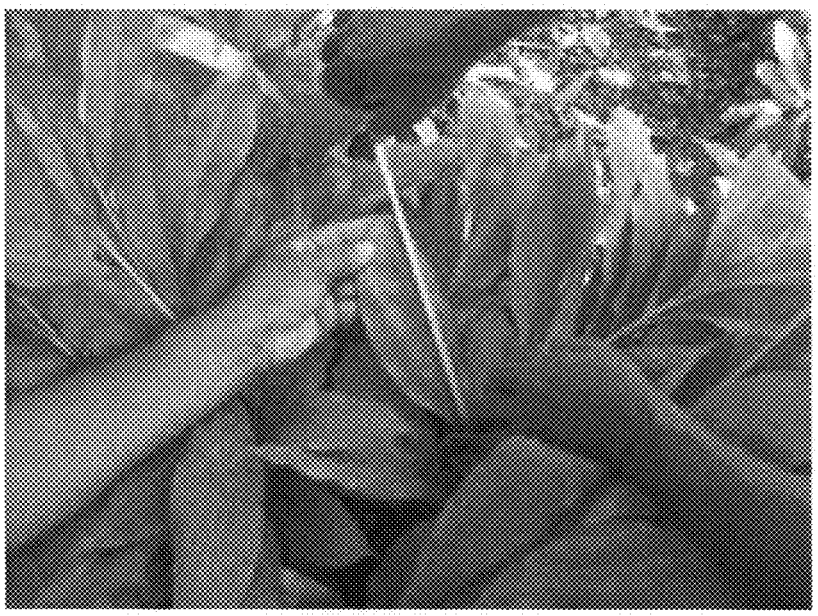
Figure 3:
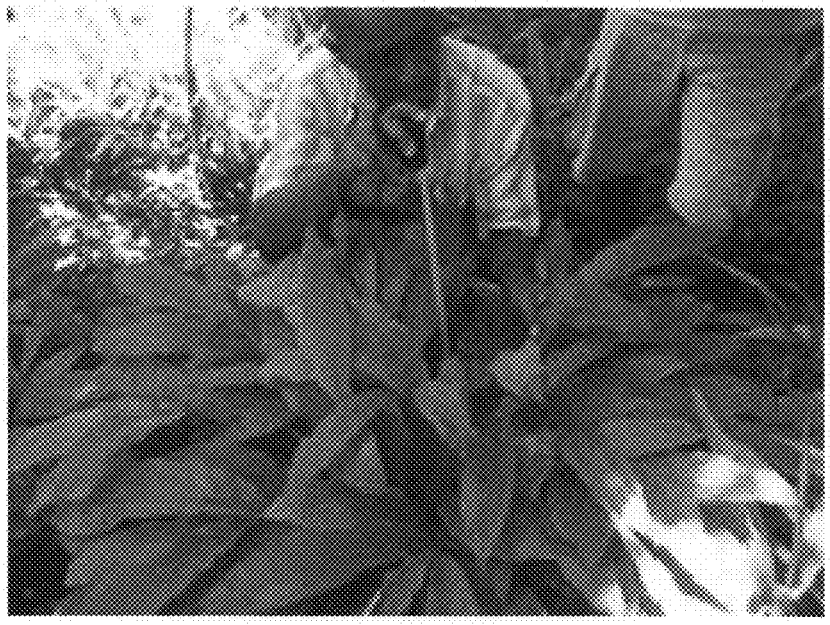
Figure 4:
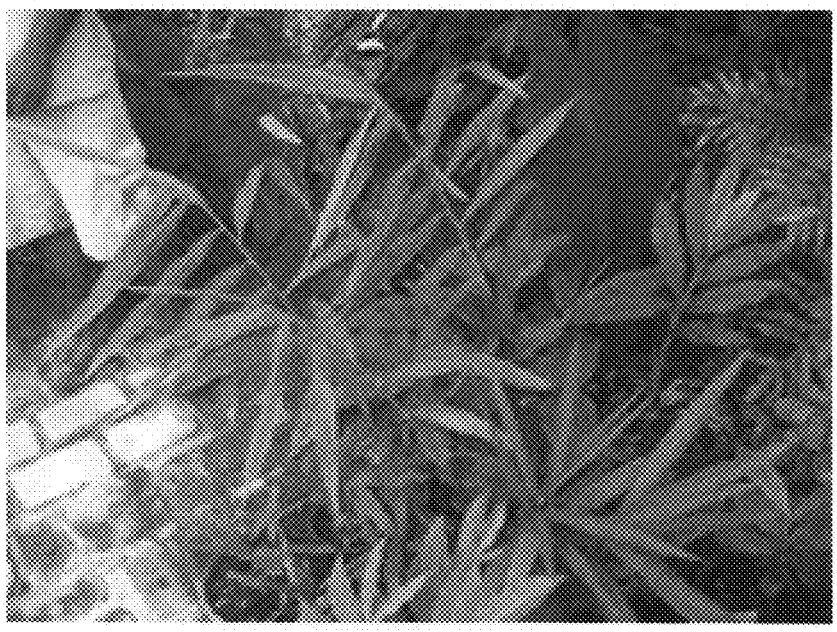
FIG. 4 shows a view of closest plant variety (*Alpinia officinarum*) to the new variety 'McghieJCG' at nine months.
Figure 5:
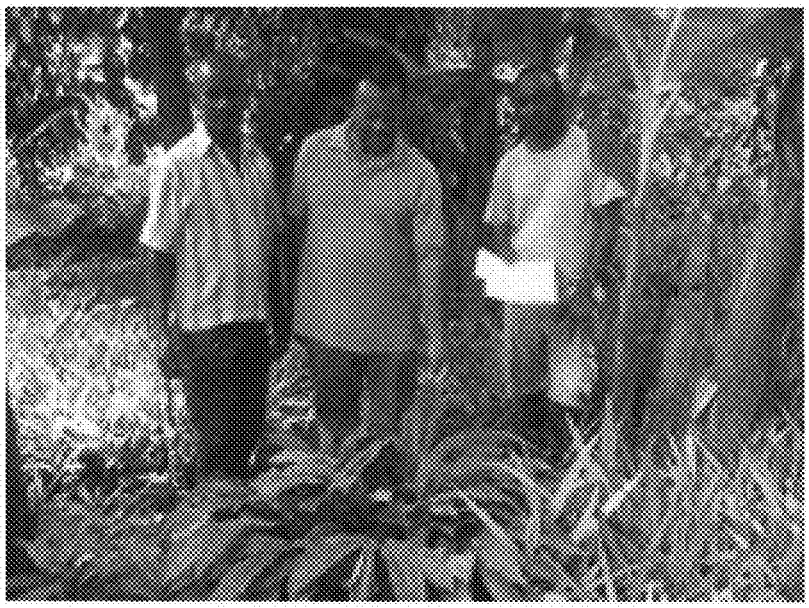
FIG. 5 shows a comparative view of the new plant variety 'McghieJCG' and *Alpinia officinarum* at nine months.
Figure 6:
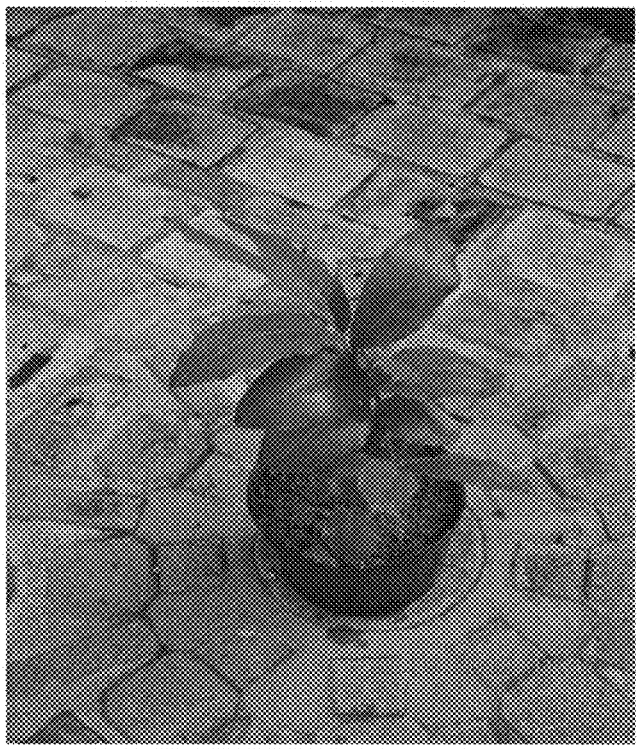
FIGS. 6 and 7 show a perspective view of the new plant variety 'McghieJCG' as potted plants.
Figure 7:
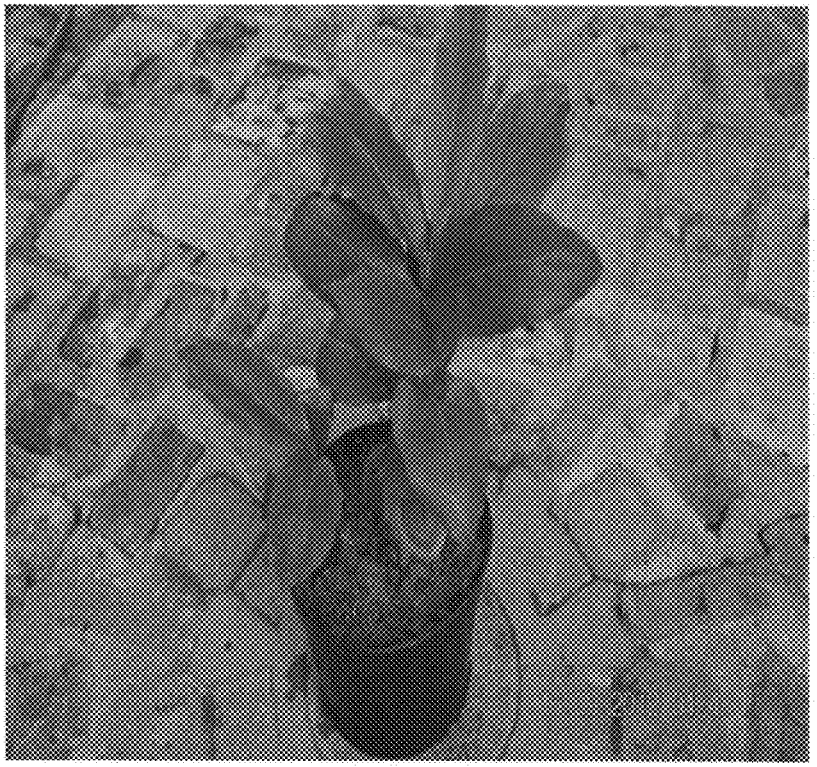
Figure 8:
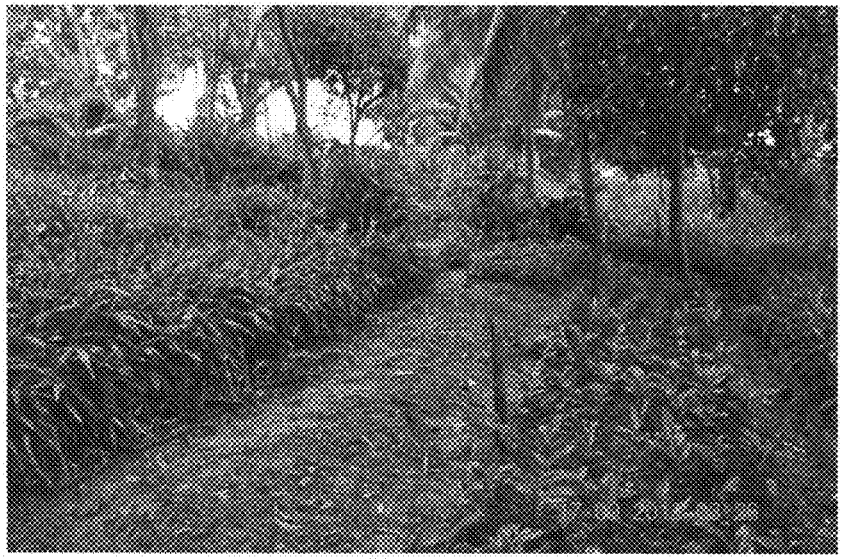
FIG. 8 shows the asexual reproduced new variety 'McghieJCG' in the center row, with *Alpinia officinarum* on the left, in a commercial nursery.
Figure 9:
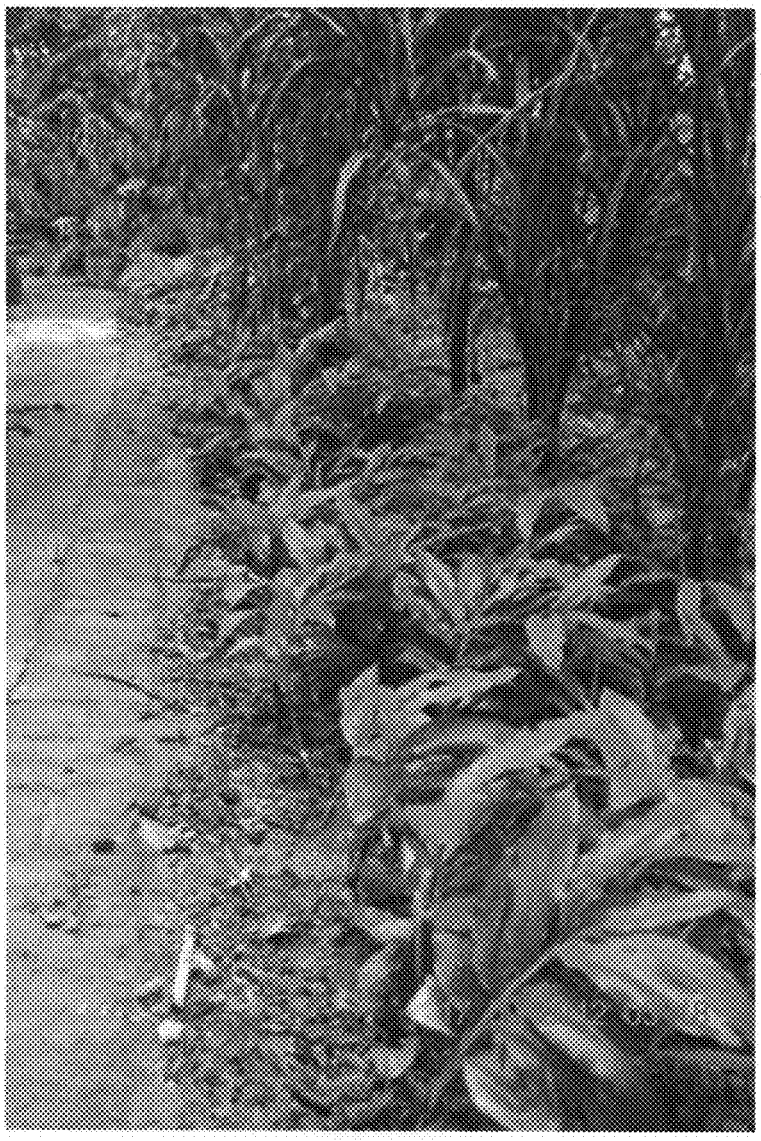
FIG. 9 shows the asexual reproduced new variety 'McghieJCG' growing in an open field in a commercial nursery.

The following is a detailed description of the new plant variety. The new variety has not been observed under all possible environmental conditions. Color designation and other values stated may deviate slightly from stated values due to seasonal changes but the deviations will be within the range expected from varying environmental conditions.

Color designations were referenced employing The Royal Horticultural Society Colour Chart ($6^{th}$ edition, 2015). The plant can be described as an 'ever green' at this stage of its growth with minimal variations in shades of (grayish olive green). This color varies according to light intensity and maturity of leaves.

The color/shade of the leaves when grown in partial lighting or direct lighting is Grayish Olive Green NN137 A.

The color/shade of the leaves when grown in no direct lighting is Grayish Olive Green NN137A.

The color/shade of the stems growing in direct lighting is Grayish Olive Green NN137A.

The color/shade of stem in partial lighting condition is Grayish Olive Green NN137B.

The following description is based on observation of the new variety at nine months growth in the open field under partial cove.

A stem cutting from the rhizome of the mother plant with the mutant attached was transplanted to a pot containing a special organic potting mixture of sandy loam soil and compost mix and placed under partial cover and grown for two months employing moderate watering. Stem cuttings from a resulting batch of six plants were obtained and transplanted to a specially prepared bed in the open field using a similar plant medium. The procedure was repeated at four months from a new batch of 42 plants. Some plants were also transplanted in specially prepared pots with a similar plant medium and placed under partial and full cover in the open field. This procedure continued at six and eight month intervals with some plants transplanted in beds with no cover. The plants were observed to grow more vigorously in the open field under partial cover especially during periods of sustained rainfall. Average growth gain observed every two months over the eight month period was eight new plants.

Origin: Stem cutting (rhizome division) Jamaica.

Parentage: *Alpinia officinarum*, lesser galangal, unknown cultivar.

Family: Zingerberacae.

Genus/species: *Languas officinarum* or *Alpinia officinarum*.

Bouquet: Aromatic and cinnamon like.

Flavor: Aromatic and cinnamon like.

Commercial: Agriculture, horticulture, herb, spice, essential oils, extracts.

Form: Perennial herb with short highly branched (rhizomes that are light yellow 18B) which eventually give rise to a high density of tillers. General vertical growth pattern of pseudo stems is dwarfed or slow in nature when compared to lesser galangal grown in similar conditions. Shoot growth of plant is generally 3-4 times shorter than that of lesser galangal at nine months. Shoot (pseudo stem) feels much more succulent and flexible when manipulated with bare hands. Shoot display heterophylly (different shapes depending on the age). Leaves are distichously.

Younger leaves: The first three to four leaves trend toward elliptic (or elliptical) with acuminate leaf apex. Average leaf is 7.5 cm in diameter times 20.7 cm long. Ligules are indistinct, or can be regarded as absent.

Later leaves: The leaves that develop after first three to four leaves. Shape is distinctly elliptic; leaf base is attenuate or very slightly etiolate (grooved petiole-1.0 cm long), and ligules are absent.

Lamina/blade: Average length for leaf shapes of the new variety is (24.4 cm), which is half that of the parent *Alpinia officinarum* (49.0 cm).

Leaf margin: Entire. Generally, leaf margins remain consistent at all stages of growth.

Leaf apex: Acuminate.

Leaf surface: Upper and lower surface are smooth.

Leaf midrib: Grooved and rounded, but not as textually pronounced as the parent plant *Alpinia officinarum*.

Leaf angle: Earlier leaves are generally oblique but as later leaves undergo elongation to be more elliptic, the angle is reduced and leaf tips bend and point downward.

Leaf sheath coloration: Very slight purple pigment on the outer upper margins (where ligules would be) extending a little beyond the point of leaf attachment.

Phyllotaxy (leaf arrangement): Alternate.

Petiole: Not distinct as they are all tightly bundled to form the pseudo stem (supporting structure of the plant).

Rhizome: Cylindrical in shape and it produces an average of 5 buds which eventually develop into mature rhizomes with their correspondent aerial pseudo stems and leaves etc.

*Average length.*—10 cm or 4 inches.

*Average width.*—1.4 cm or ½ inch.

Fragrance description: Fragrance of leaves may be described as a moderate spicy fragrant blend of leaf cinnamon, ginger and lemon (with no lingering sensation or feeling on nasal and throat mucosa).

Leaf fragrance detection: Held closely to the nostrils without rubbing or crushing of green excised leaves, the emanated fragrance is detected readily from the upper surface of the leaf. This is in contrast to lesser galangal in which fragrance is detected less readily as coming from the opposite/reverse side of the leaf. When leaf is manipulated (crushed) or cut there is a pungent cinnamon fragrance that emanates from the leaf with traces of other fragrances. These fragrances are more pronounced in the leaves of plants grown in higher light intensities.

Flowers, fruit, seeds and reproductive organs have not been observed with the new variety to date.

A comparison of the growth of 'McghieJCG' vs the *Alpinia officinarum* grown in the Jamaican humid tropics is shown in Table 1. Both plants were nine months old.

TABLE 1

'McghieJCG' vs. lesser galangal at nine months

| Parameter | 'McghieJCG' (cm) | *Alpinia officinarum* (cm) |
|---|---|---|
| Average leaf length (Upper*) | (28.12) 11.2 inches | (47) 18.8 inches |
| Average leaf length (Lower**) | (20 .75) 8.3 inches | (51) 20.4 inches |
| Average leaf width (Upper) | (6.5) 2.6 inches | (6.00) 2.4 inches |
| Average leaf width (Lower) | (7.5) 3 inches | (7.00) 2.8 inches |
| Average leaf shoot height | (47) 18.8 inches | (163) 65.2 inches |
| Stool (mat) Diameter (Canopy to leaf tip). | (140) 56 inches | N/A |

*Measurement from the Apex of the leaf, sheath of the third fully formed (expanded) leaf from the top down

** Measured at the 6th leaf from the upper leaf. Invariable the 6$^{th}$ leaf was different from the upper leafs.

The leaf of *Alpinia officinarum* is linear, and never shows heterophylly. Its ligule is very distinct (2.5 cm-3 cm long). Shoot growth is generally 3-4 times taller in comparison to the 'McghieJCG' at nine months. The shoot (pseudo stem) appears much more fibrous (tough) and less succulent than 'McghieJCG'.

ECOLOGICAL & ENVIRONMENTAL CONDITIONS RELEVANT TO THE GROWTH OF THE NEW PLANT VARIETY

Temperature—Daytime temperature ranges from 21° C.-32° C. (70° F.-90° F.), with lower temperatures during the cool seasons and nights.

Humidity—Relative humidity ranges from 85-95%.

Rainfall—Annual rain fall averages from 2000 mn-2500 mm (80-100 inches) and is evenly distributed throughout each year. The observation of the adequately fertilized plants may deviate in varying degrees from the stated parameters of the potted plants at specified periods of growth, but the deviations will be in the range expected from the varying environmental, seasonal and collateral conditions.

Soil type—Sandy and clay loam.

Habitat—The cultivated field serves as a dual purpose home garden and commercial nursery.

Other plants grown in the same habitat: Ginger family-Varying herbs/spices namely, Turmeric, Curcuma, *Alpinia galangal* and *Alpinia officinarum. Kempheria galangal, Alpinia purpurata* and miscellaneous plants of other families e.g., young cinnamon trees, bananas, citrus, plantains, mint, fever grass, and other agricultural perennials.

DEFINITIONS AND NOTIONS TO THE ABOVE DESCRIPTIONS

Elliptic: Broadest at the middle, with length usually more than twice the width.

Accumulates: A gradually tapering to a prolonged point with two margins pinches slightly before reaching the tip. The tip maybe short or long and narrow or broad.

Glabrous: No hair present; smooth and free hairs.

Leaf measurement: This was taken pseudostems from (a). The third fully formed leaf (from short apex) and (b) the sixth leaf from the form.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claim. I therefore claim as my invention all that comes within the scope and spirit of this claim.

I claim:

1. A new and distinct *Alpinia officinarum* plant as herein illustrated and described.

* * * * *